United States Patent [19]
Reinhard et al.

[11] Patent Number: 5,878,917
[45] Date of Patent: Mar. 9, 1999

[54] DEVICE FOR ADMINISTERING SUBSTANCES SUCH AS AN INHALATION PREPARATION

[75] Inventors: Michael Reinhard, Ober-Olm; Ralf Bouffleur, Bad Kreuznach; Michael Spallek, Ingelheim; Andreas Geiger, Wörrstadt, all of Germany

[73] Assignee: Schott Glas, Mainz, Germany

[21] Appl. No.: 678,857

[22] Filed: Jul. 12, 1996

[30] Foreign Application Priority Data

Jul. 13, 1995 [DE] Germany .......................... 195 25 546.1

[51] Int. Cl.[6] ...................................................... B67D 5/64
[52] U.S. Cl. ............................ 222/156; 222/162; 222/183
[58] Field of Search .................................... 222/162, 156, 222/158, 183

[56] References Cited

U.S. PATENT DOCUMENTS 3,184,115  5/1965  Meshberg .
3,432,072  3/1969  Quercia .
3,968,871  7/1976  Briscoe .

FOREIGN PATENT DOCUMENTS 9113446      2/1992   Germany .
295 11 334  12/1995   Germany .
WO 89/06793  7/1989   WIPO .
WO 92/09323  6/1992   WIPO .

*Primary Examiner*—Gregory L. Huson
*Attorney, Agent, or Firm*—Walter Ottesen

[57] ABSTRACT

The invention relates to a device for administering substances at overpressure. The device includes a pressure vessel made of glass and containing a substance to be discharged from the pressure vessel and at least one propellent. The pressure vessel has an opening and an actuable discharge element mounted on the pressure vessel in the opening for releasing the substance from the pressure vessel. A self-supporting housing encloses the pressure vessel and at least a portion of the discharge element to prevent splinters of glass and the discharge element from being propelled away from the device in the event that the pressure vessel bursts. The self-supporting housing has a lower portion made of transparent plastic to facilitate viewing the substance in the pressure vessel.

18 Claims, 2 Drawing Sheets

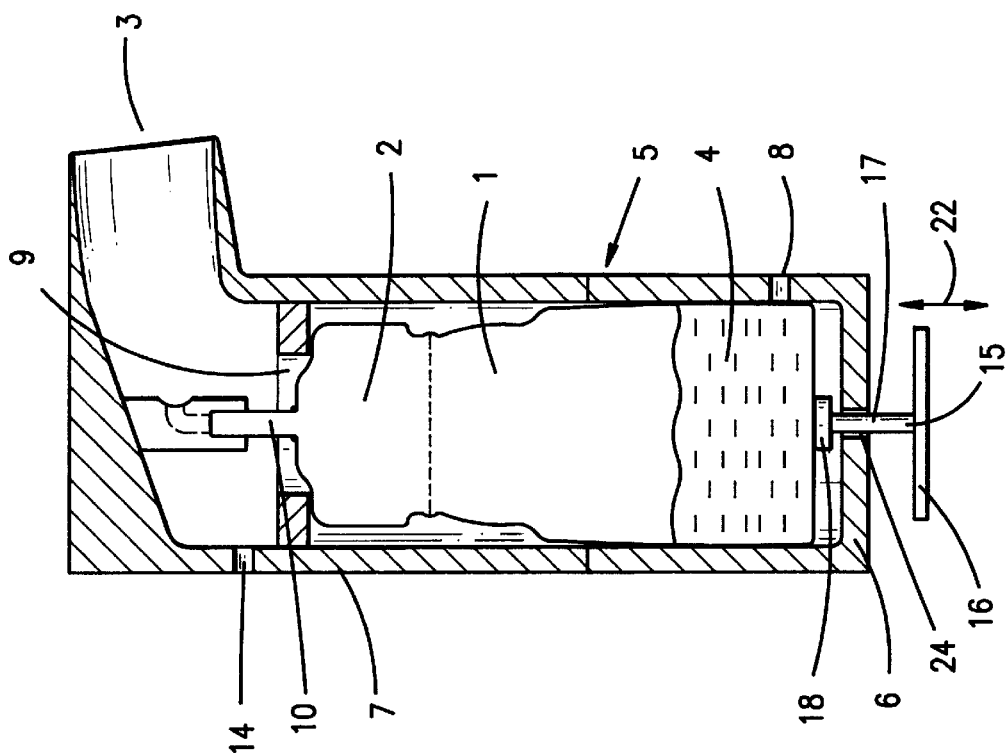

DEVICE FOR ADMINISTERING SUBSTANCES SUCH AS AN INHALATION PREPARATION

FIELD OF THE INVENTION

The invention relates to a device for administering substances such as inhalation preparations (aerosols) with overpressure and includes a pressure vessel made of glass which contains a supply of at least one substance to be emitted and at least one propellent. The device includes an outlet opening whereat a discharge element is attached. Plastic surrounds the pressure vessel and provides protection against bursting and splintering. A delivery head coacts with the discharge element so that the discharge element is actuated when the two parts are pressed toward each other. A specific quantity of the least one substance to be supplied passes through the outlet opening and is ejected in the form of at least a spray from a discharge opening of the delivery head.

BACKGROUND OF THE INVENTION

The pressure vessel of the above-described device is in the form of a small bottle. The volume of the bottle can be 5 to 50 ml. The outlet opening is provided at the upper end of the bottle. This outlet opening is, as a rule, closed by pressing a discharge element into the opening and/or by flange connecting the discharge element to the pressure vessel, for example, a metering valve having an upwardly projecting cylindrical hollow needle often with an elastic seal arranged between the head and the metering valve.

The pressure vessel is filled in such a manner that the substance to be emitted is first introduced through the metering valve or is introduced through the metering valve together with the propellent.

As preparation for administering, the pressure vessel is pushed into a cylindrical part having a delivery head. The cylindrical hollow needle of the metering valve is introduced form-tight into a cylindrical receptacle of the delivery head. The receptacle is hollow and communicates with a channel. As a rule, the channel opens into an opening which is in the end of the delivery head and is configured as a spray head.

The delivery head can have a mouth or nose piece which can be protected against contamination with the aid of a cap mounted thereon.

In the known device, the pressure vessel projects with the delivery head from the bottom of the cylindrical part.

The metering valve can be activated in that the user presses from above with the index finger against the delivery head and against the pressure vessel with the thumb from below. This then triggers the metering valve thereby emitting a defined quantity of active substances via the nozzle head.

The known pressure vessel made of glass is covered with a coating of a transparent plastic. This coating is intended to protect against splinters when the vessel bursts and therefore comprises a flexible soft plastic, such as PVC having a high expansion. The high expansion is important because the inner pressure acts on the soft plastic in the case that the glass vessel bursts. If the soft plastic could not yield with a change in volume in response to the pressure, then a sudden destruction of the plastic material could well occur because of disintegration or corrosion stress cracking.

The known arrangement affords the advantage that it permits a visual determination of the residual quantity in the pressure vessel of the substance to be supplied. This is so because both the pressure vessel and the enclosure are made of a transparent material (glass). This is of special significance in the administration of inhalation preparations which often have the nature of an emergency medication (for example, an asthma preparation). In this connection, the danger would otherwise be present that the pressure vessel could be empty in the event of an emergency.

In the known arrangement, it is disadvantageous that the transparent pressure vessel of glass is not sufficiently safe notwithstanding a coating with plastic in the case of an explosion, for example, because of incorrect handling. This insufficient degree of safety is present because the coating cannot prevent parts of the glass vessel from being propelled into the ambient in the manner of a projectile, especially in the region of the valve.

It is furthermore known to utilize pressure vessels made of metal materials. The bursting and splintering protection for such pressure vessels is effected by the advantageous characteristics of the selected material. These characteristics include high toughness and high strength.

It is a disadvantage of this device, however, that the opaque pressure vessel permits no visual determination of the residual quantity of the substance to be supplied which, in turn, brings with it the above-described disadvantages.

SUMMARY OF THE INVENTION

It is an object of the invention to improve a pressure vessel of the kind described above so that advantage is retained of permitting a visual determination of the residual quantity of the substance in the pressure vessel and which is to be supplied while, on the other hand, significantly increasing the protection against bursting and splinters when compared to known vessels.

The device of the invention is for administering substances at overpressure. The device includes a pressure vessel made of glass and containing a substance to be discharged from the pressure vessel and at least one propellent. The pressure vessel has an opening and an actuable discharge element is mounted on the pressure vessel in the opening for releasing the substance from the pressure vessel when actuated. A self-supporting housing encloses the pressure vessel and at least a portion of the discharge element to prevent splinters of glass and the discharge element from being propelled away from the device in the event that the pressure vessel bursts. The self-supporting housing has a lower portion made of transparent plastic to facilitate viewing the substance in the pressure vessel.

Thus, according to this invention, the pressure vessel is completely enclosed by a housing and the housing also surrounds the discharge element with the exception of the discharge opening. In this way, it is ensured that neither splinters nor the discharge element (for example, a metering valve) can be propelled outwardly in the manner of a projectile.

The housing and the pressure vessel of the device of the invention are not in fixed surface-to-surface contact with each other, that is, the housing and pressure vessel do not conjointly define a bond or composite. This affords the advantage compared to the use of a plastic jacket that fissures which occur in the plastic cannot migrate into the glass wall of the pressure vessel as in the case of the known device. In the known device, this migration can cause the glass pressure vessel to burst. Accordingly, the glass vessel of the invention retains its original strength and increased protection against bursting is provided.

The device according to the invention is also conveniently recycled because the glass vessel and plastic housing are easily separated from each other.

According to the invention, the plastic housing is made of a transparent plastic, at least in the lower portion of the pressure vessel. The user can then determine at any time whether the supply of the substance to be outputted is almost gone and take the necessary steps.

The increased protection against splintering and bursting provided by the invention permits even thin-walled pressure vessels to be used. For example, where the device of the invention is used as an applicator for inhalation preparations, pharmaceutical vessels made of glass tubes can be used having a wall thickness reduced up to 40% in comparison to known applicators having glass pressure vessels. This leads to a saving of material when producing the pressure vessel for the applicator of the invention. Conventional filling devices can be used because the pressure vessel in the solution of the invention does not change with respect to its dimensions compared to known applicators.

A further advantage of the invention is that the penetration of foreign bodies between the pressure vessel and the housing is made significantly more difficult. In this way, the danger is reduced that foreign bodies will be inhaled from this region, especially for the above-mentioned application.

A plastic, which is suitable for producing the housing for the device of the invention, must have the following characteristics: transparency, high toughness to shock and becoming elongated upon breakage or fracture. The following materials are preferred: polycarbonate, polyethylene terephthalate and amorphus polyamide.

Preferably, the housing is formed of two half shells, for example, an upper and a lower half shell. These half shells are joined to each other after the pressure vessel is placed therein. On the one hand, this affords the advantage that the lower half shell can be joined to the glass vessel directly after production thereof. In this way, the base region of the pressure vessel, which is subjected the most to pressure loads, is protected against surface defects which reduce strength and the high tensile strength of the glass is maintained. On the other hand, and because of the configuration in two half shells, the delivery element can be first mounted on the vessel and thereafter the half shells can be mounted and joined so that the half shells conjointly form a safety container about the glass vessel having the discharge element.

With the above-described two part configuration, the lower half shell can be made of a transparent plastic and the upper half shell can, in contrast, be made of a colored plastic to facilitate marking. For example, for applicators for inhalation preparations, the upper half shell can be provided with instructions for use of the pressure vessel for different medications.

The half shells can be joined to each other utilizing mechanical, physical or chemical methods. The connection is achieved, for example, utilizing ultrasound welding, friction welding, heat welding, adhesive or mechanical engagement utilizing specially formed edges of the half shells. This effects a tight connection of the half shells to each other.

A releasable connection is preferred because this facilitates separate recycling of glass and plastic.

In a preferred embodiment, the two half shells are hooked to each other by means of counter hooks which can be pushed one over the other. This affords the advantage that the complexity of the apparatus for this connecting system is substantially reduced and the manufacturing costs for a device of the invention are held low. It should be noted that the connection has a minimum tensile strength computed from the following formula:

$$\sigma_m = 2.0 \text{MPa} \times (d_a - s)/(2 \times s)$$

$\sigma_m$=minimum tensile strength of the connection in megaPascal (MPa)

$d_a$=outer diameter of the hollow body (mm)

s=wall thickness of the hollow body (mm)

(With respect to the above, 2.0 MPa corresponds to an internal pressure of 20 bar.)

The housing is provided with pressure venting openings in accordance with an embodiment of the device of the invention. In the case where the pressure vessel bursts, the substance to be discharged and the propellant can escape through these pressure venting openings. In this way, the contents of the pressure vessel can exit from the housing and the danger of a chemical attack by the material held in the pressure vessel on the housing material (stress corrosion cracking) and therefore the danger of explosion is further reduced.

The housing can have a system of channels in its inner wall, that is grooves, which function to conduct the contents of the vessel as rapidly as possible through the channels to the pressure venting openings in the case where the vessel bursts. In this embodiment, the housing can lie directly against the wall of the pressure vessel without pressure building up at any location in the housing when the vessel bursts. The system of channels can also be defined by a plurality of splines formed on the inner wall surface of the housing.

BRIEF DESCRIPTION OF THE DRAWINGS

The invention will now be described with reference to the drawings wherein:

FIG. 2 is a side elevation view, in section, of a second embodiment of the applicator according to the invention; and, FIG. 3 is a side elevation view, in section, of a third embodiment of the applicator of the invention.

DESCRIPTION OF THE PREFERRED EMBODIMENTS OF THE INVENTION

Figure 1B:
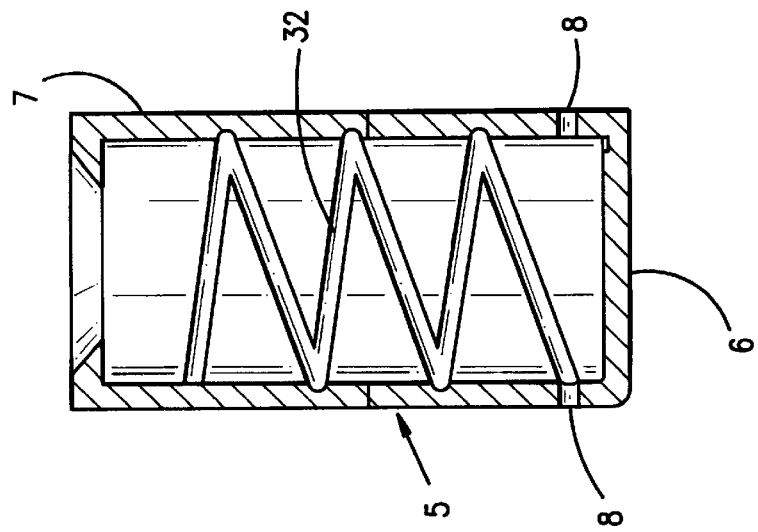
FIG. 1b is a schematic showing channels having a spiral configuration formed in the inner wall surface of the housing of the embodiment shown in FIG. 1.
Figure 1A:
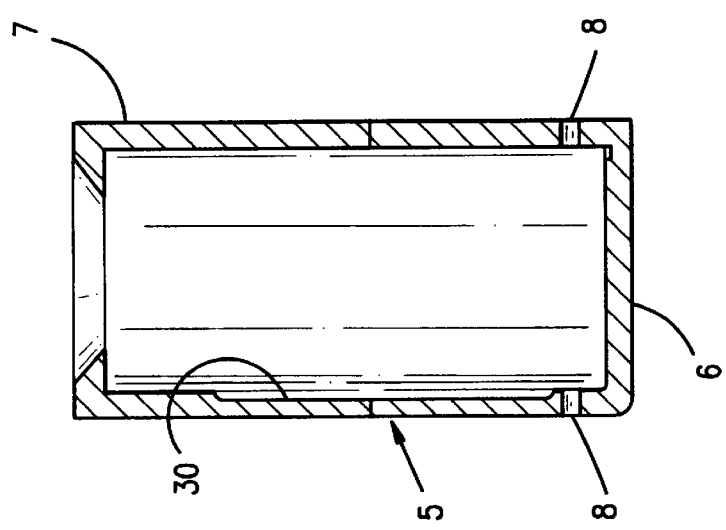
FIG. 1a is a schematic showing a channel formed in the inner wall surface of the housing shown in FIG. 1.
Figure 1:
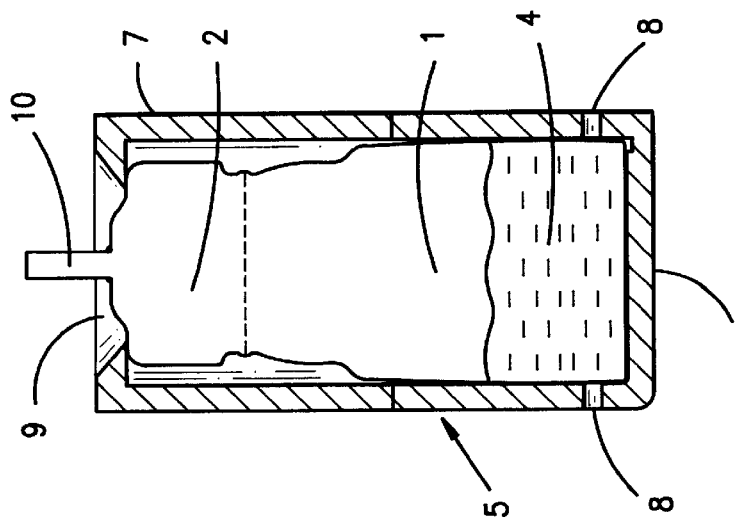
FIG. 1 is a side elevation view, in section, of an embodiment of the device according to a first embodiment of the invention wherein a pressure vessel of glass having a metering valve is completely surrounded by a self-supporting housing.

In FIG. 1, the pressure vessel 1 is for an applicator for an inhalation preparation and is made of glass, for example, borosilicate glass or soda-lime glass. The base region of the pressure vessel 1 is preferably outwardly hemispherically shaped in order to reduce occurring tensile stresses to a minimum. The pressure vessel 1 has a discharge element in the form of a metering valve 2 which is attached by crimping and/or is flanged in the region of the discharge opening. An aerosol 4 is disposed in the pressure vessel 1 and is filled therein under pressure.

According to the invention, the pressure vessel 1 is virtually completely surrounded by a housing 5. The housing 5 is configured to have two parts in the embodiment of FIG. 1. The housing 5 includes a lower half shell 6 and an upper half shell 7. As shown, the housing 5 surrounds the metering valve 2 in the upper region of the pressure vessel 1 to the extent that the valve cannot be accelerated away from the vessel 1. The lower half shell 6 is a cylindrically shaped part made of transparent plastic and is preferably made of polycarbonate or polyethylene terephtalate. The form part 6 is so configured that it can be pushed form-fitting over the lower part of the housing. Pressure venting openings 8 are integrated into the lower half shell 6 in such a manner that the contents of the vessel, when suddenly released because of a rupture of the pressure vessel, can escape without damaging the housing 5. The pressure venting openings 8 can be, for example, in the form of lateral slots or holes in the base region.

At the same time, a system of channels 30 (FIG. 1a) in the interior of the half shell 6 ensures that the vessel contents 4, which are under pressure, are conducted as rapidly as possible to the openings 8 and reach the ambient in the event that the pressure vessel 1 bursts. The openings 8 are so small that no glass splinters can pass therethrough which could injure persons.

According to another embodiment, the channels can be formed in the inner wall surface of the housing 5 so as to have the spiral configuration 32 shown in FIG. 1b.

The upper half shell 7 is likewise a cylindrical or a round form part made of transparent or nontransparent plastic. This form part preferably has the same peripheral dimensions as the lower half shell 6. The upper half shell 7 is so dimensioned that it can be pushed form-fitting over the upper part of the pressure vessel 1 to which the metering valve 2 has already been crimped and/or flange connected.

At least one opening 9 is provided in the upper half shell 7 which is sufficiently large in order to facilitate passing the valve shaft 10 or other valve parts therethrough.

Preferred embodiments of the applicator of the invention are shown in FIGS. 2 and 3.

In both FIGS. 2 and 3, the delivery head is identified by reference numeral 11 and, in these embodiments, is a mouthpiece defining a discharge opening 3. The delivery head has a cylindrical receptacle for the valve shaft 10 of the metering valve 2. The configuration of the pressure vessel 1 with the housing 5 corresponds approximately to that shown in FIG. 1.

The delivery head 11 is held on the housing 5 in both embodiments. This type of mounting has especially the advantage that the valve shaft 10 of the metering valve 2 is protected against mechanical load and clogging by dirt particles.

The delivery head 11 is advantageously connected so securely to the housing 5 that it cannot separate during normal use. In this way, the applicator is ready for use at any time. Two different variations for such a connection are shown in FIGS. 2 and 3, respectively.

In FIG. 2, the delivery head 11 is pressed from above on the housing 5 and anchored in this position. For this purpose, the delivery head 11 has inwardly directed hooks 12 at its lower end which engage in corresponding slots 13 formed in the housing wall. The slots 13 extend longitudinally in order to permit a vertical movement of the discharge head 11 for making possible an actuation the metering valve 2. Arrow 20 indicates the direction of movement to actuate the metering valve 2. The metering valve 2 is triggered by pressing down the delivery head 11, whereby a defined amount of effective material is released via the nozzle opening. After the substance is administered, the delivery head 11 is again returned to its start position by the spring force of the metering valve 2.

In FIG. 2, the delivery head has ventilating and venting openings 14 which are so configured that an unwanted closure by the user is precluded. Thus, the openings 14 are so placed that the user will not inadvertently block the openings when holding the applicator in the hand. The openings 14 permit air to enter the mouthpiece 11 and mix with the substance 4 as it is discharged via metering valve 2. The released substance and the incoming air conjointly form a mist-like spray which the user inhales.

In the embodiment of FIG. 3, the delivery head 11 is connected rigidly to the housing 5, for example, by means of ultrasonic welding. In this embodiment, the metering valve 2 is triggered by an activating unit 15 operating from below on the base of the pressure vessel.

With the aid of the activating unit 15, the pressure vessel 1 is moved vertically within the housing 5 as indicated by arrow 22 thereby actuating the metering valve 2. The housing 5 must have a length greater than the housing shown in FIG. 2 by an amount equal to the length of the valve actuating path to ensure operation of the device.

The activating unit 15 comprises a finger support 16 and a stem 17 extending therefrom and projecting into the housing 5. The stem 17 has a thickening 18 having a diameter greater than the diameter of the passthrough opening 24.

Inside the housing 5, the pressure vessel 1 is seated with its base on the activating unit 15. For administering the medicine, the support 16 is pressed against the housing 5. Thereafter, the thickening 18 presses against the base of the pressure vessel 1 which is then displaced upwardly against the spring pressure of the metering valve 2 so that the cylindrical hollow tube 10 of the metering valve 2 is pressed against the cylindrical receptacle of the delivery head 11 thereby triggering the metering valve 2.

It is understood that the foregoing description is that of the preferred embodiments of the invention and that various changes and modifications may be made thereto without departing from the spirit and scope of the invention as defined in the appended claims.

What is claimed is:

1. A device for administering substances at overpressure, the device comprising:

an aerosol pressure vessel made of glass and containing a substance to be discharged from said pressure vessel and at least one propellant;

said pressure vessel having an opening;

an actuable discharge element mounted on said pressure vessel in said opening for releasing said substance from said pressure vessel when actuated;

a self-supporting housing enclosing said pressure vessel and at least a portion of said discharge element to prevent splinters of glass and said discharge element from being propelled away from said device in the event that said pressure vessel bursts; and, said self-supporting housing having a lower portion made of transparent plastic to facilitate viewing said substance in said pressure vessel.

2. The device of claim 1, said self-supporting housing including a lower half shell and an upper half shell; and, said lower half shell being made of said transparent plastic.

3. The device of claim 2, said upper half shell being made of a colored plastic on which a specific medication is marked.

4. The device of claim 2, said upper half shell having a color marking for identifying a specific medication.

5. The device of claim 2, said half shells conjointly defining connecting means for releasably connecting said half shells to each other.

6. The device of claim 5, said connecting means comprising counter hooks slidable over each other to hook said half shells together.

7. The device of claim 1, said housing having pressure venting openings formed therein.

8. A device for administering substances at overpressure, the device comprising:
- a pressure vessel made of glass and containing a substance to be discharged from said pressure vessel and at least one propellent;
- said pressure vessel having an opening;
- an actuable discharge element mounted on said pressure vessel in said opening for releasing said substance from said pressure vessel when actuated;
- a self-supporting housing enclosing said pressure vessel and at least a portion of said discharge element to prevent splinters of glass and said discharge element from being propelled away from said device in the event that said pressure vessel bursts;
- said self-supporting housing having a lower portion made of transparent plastic to facilitate viewing said substance in said pressure vessel;
- said housing having pressure vent openings formed therein; and,
- said housing having an inner wall surface and channels formed in said inner wall surface for conducting said substance and said propellent directly to said pressure vent openings in the event said pressure vessel bursts.

9. The device of claim 8, said channels being formed in said inner wall surface so as to have a spiral configuration.

10. The device of claim 1, said self-supporting housing including a main portion, which includes said lower portion; and, a delivery head defining a discharge opening; and, said delivery head being mounted so as to be held on said main portion.

11. The device of claim 10, said housing defining a longitudinal axis; said delivery head being fixedly connected to said main portion of said housing; and, said pressure vessel being displaceable in said housing along said axis for actuating said discharge element.

12. The device of claim 11, said pressure vessel having a base; and, said device further comprising an activating unit mounted on said lower end portion for displacing said pressure vessel within said housing to activate discharge element.

13. The device of claim 10, said housing defining a longitudinal axis; and, said pressure vessel being fixedly positioned in said housing; and, said delivery head being held on said main portion so as to be displaceable along said axis to actuate said discharge element.

14. The device of claim 13, said main portion having an outer wall surface and a plurality of slots formed therein; and, said delivery head having a plurality of inwardly directed hooks formed at the lower end thereof for engaging said slots, respectively.

15. The device of claim 1, wherein said lower portion of said self-supporting housing is made entirely of transparent plastic.

16. A device for administering substances at overpressure, the device comprising:
- an aerosol pressure vessel made of glass and containing a substance to be discharged from said pressure vessel and at least one propellent;
- said pressure vessel having an opening;
- an actuable discharge element mounted on said pressure vessel in said opening for releasing said substance from said pressure vessel when actuated;
- a self-supporting housing enclosing said pressure vessel and at least a portion of said discharge element to prevent splinters of glass and said discharge element from being propelled away from said device in the event that said pressure vessel bursts;
- said self-supporting housing having a lower portion made of transparent plastic to facilitate viewing said substance in said pressure vessel;
- said self-supporting housing defining a longitudinal axis and including a main portion defined by said lower portion; and, a delivery head defining a discharge opening arranged along a transverse axis substantially perpendicular to said longitudinal axis;
- said delivery head being mounted so as to be held on said main portion; and,
- a venting opening formed in said delivery head opposite said discharge opening and rearward of said actuable discharge element whereby air enters said delivery head via said venting opening and mixes with the substance discharged from said pressure vessel to form a mist-like spray.

17. A device for administering substances at overpressure, the device comprising:
- an aerosol pressure vessel made of glass and containing a substance to be discharged from said pressure vessel and at least one propellent;
- said pressure vessel having an opening;
- an actuable discharge element mounted on said pressure vessel in said opening for releasing said substance from said pressure vessel when actuated;
- a self-supporting housing defining a longitudinal axis and enclosing said pressure vessel and at least a portion of said discharge element to prevent splinters of glass and said discharge element from being propelled away from said device in the event that said pressure vessel bursts;
- said self-supporting housing consisting only of two housing parts: a lower portion made of transparent plastic to facilitate viewing said substance in said pressure vessel; and, a delivery head movably mounted on said lower portion so as to be displaceable a predetermined distance along said axis to actuate said discharge element; and,
- connecting means for securely holding said delivery head on said lower portion while at the same time permitting said delivery head to be displaced along said axis by said predetermined distance.

18. The device of claim 17, said lower portion having an outer wall surface and said connecting means including a plurality of slots formed in said outer wall surface; and, said delivery head having a plurality of inwardly directed hooks formed at the lower end thereof for engaging said slots, respectively.

* * * * *